(12) United States Patent
Sander-Tavallaey et al.

(10) Patent No.: US 10,539,499 B2
(45) Date of Patent: Jan. 21, 2020

(54) CONDITION MONITORING OF AN INDUSTRIAL ROBOT

(71) Applicant: ABB Research Ltd., Zurich (CH)

(72) Inventors: Shiva Sander-Tavallaey, Taby (SE); Kari Saarinen, Vasteras (SE); Hans Andersson, Vasteras (SE); Andre Carvalho Bittencourt, Linkoping (SE)

(73) Assignee: ABB Research Ltd., Zurich (CH)

( * ) Notice: Subject to any disclaimer, the term of this patent is extended or adjusted under 35 U.S.C. 154(b) by 574 days.

(21) Appl. No.: 14/224,752

(22) Filed: Mar. 25, 2014

(65) Prior Publication Data

US 2014/0222352 A1     Aug. 7, 2014

Related U.S. Application Data

(63) Continuation of application No. PCT/EP2012/069318, filed on Oct. 1, 2012.

(60) Provisional application No. 61/542,589, filed on Oct. 3, 2011.

(51) Int. Cl.
   *G01B 5/28*      (2006.01)
   *G01N 19/08*     (2006.01)
   *B25J 9/16*      (2006.01)

(52) U.S. Cl.
   CPC ............ *G01N 19/08* (2013.01); *B25J 9/1674* (2013.01); *G05B 2219/37256* (2013.01); *G05B 2219/37344* (2013.01); *G05B 2219/40335* (2013.01); *Y10S 901/46* (2013.01)

(58) Field of Classification Search
   CPC .......... G05B 19/00; G05B 2219/37246; G05B 2219/37254; G05B 2219/37344; G05B 2219/42304; G05B 2219/37457; G05B 2219/40335; G05B 2219/37256; G01N 19/08
   USPC .......... 702/35, 33, 34, 44, 41, 183; 700/245; 318/434
   See application file for complete search history.

(56) References Cited

U.S. PATENT DOCUMENTS

| | | | |
|---|---|---|---|
| 3,694,637 A | 9/1972 | Edwin et al. | |
| 6,275,765 B1 * | 8/2001 | Divljakovic | G01M 15/05 701/102 |
| 7,715,992 B2 | 5/2010 | Kashio et al. | |
| 2005/0278148 A1 | 12/2005 | Bader et al. | |

(Continued)

OTHER PUBLICATIONS

Labrosse et al, "Embededed Software" (2008).*

(Continued)

*Primary Examiner* — Sujoy K Kundu
*Assistant Examiner* — Xiuqin Sun
(74) *Attorney, Agent, or Firm* — Whitmyer IP Group LLC

(57) ABSTRACT

A method for detecting a fault in a robot joint includes the steps of: performing a first torque measurement at the robot joint to thereby obtain a first set of torque values; calculating a first distribution characteristic reflecting a distribution of the first set of torque values; performing a second torque measurement at the robot joint to thereby obtain a second set of torque values; calculating a second distribution characteristic reflecting a distribution of the second set of torque values; and comparing the first and the second distribution characteristics to determine whether a fault is present or not. A difference in the distributions of torque measurements is a robust fault indicator that makes use of the repetitive behavior of the system.

17 Claims, 3 Drawing Sheets

(56) References Cited

U.S. PATENT DOCUMENTS

2008/0133176 A1* 6/2008 Kashio et al. ............... 702/183
2009/0146601 A1 6/2009 Le
2010/0153025 A1* 6/2010 Ling ........................ F02C 9/00
   702/41
2011/0257901 A1* 10/2011 Bechhoefer .............. G01H 1/00
   702/34

OTHER PUBLICATIONS

Kim et al., "Robust Kernel density estimation" (Sep. 2011).*
International Preliminary Report on Patentability Application No. PCT/EP2012/069318 dated Dec. 18, 2013 18 pages.
International Search Report & Written Opinion of the International Searching Authority Application No. PCT/EP2012/069318 Completed: Feb. 11, 2013; dated Feb. 18, 2013 12 pages.
Bittencourt, et al. "Modeling and Identification of Wear in a Robot Joint Under Temperature Uncertainties"; Technical Report; Oct. 11, 2010; 9 pages.
Written Opinion of the International Preliminary Examining Authority Application No. PCT/EP2012/069318 dated Sep. 9, 2013 8 pages.

* cited by examiner

CONDITION MONITORING OF AN INDUSTRIAL ROBOT

FIELD OF THE INVENTION

The present invention relates to a method for detecting a fault in a robot joint.

BACKGROUND OF THE INVENTION

In the manufacturing industry making use of industrial robots, preventive scheduled maintenance of the robots is a common approach used to improve equipment safety, reliability, availability and maintainability. This setup delivers high availability, reducing operational costs (e.g. small downtimes) with the drawback of high maintenance costs since unnecessary maintenance actions might take place. Condition based maintenance, "maintenance when required", can deliver a good compromise between maintenance costs and operational costs, reducing the overall costs. The extra challenge of condition based maintenance is to define methods to determine the condition of the equipment. Preferably, this should be done automatically.

Conventionally in robotics, condition monitoring and fault detection methods are mainly considered in the time-domain, the use of nonlinear observers being a typical approach in many of the known methods. It is known for example to diagnose the condition of an industrial robot by monitoring friction in the robot joints. Since friction does not only depend on wear but also other phenomena such as speed, load and temperature, this approach assumes a known friction model taking these factors into account. In practice it is, however, difficult to construct an accurate friction model which can describe the effects of speed, load, temperature and wear.

A desire remains to provide a more robust condition monitoring method for an industrial robot.

SUMMARY OF THE INVENTION

One object of the invention is to provide a more robust method for detecting a fault in a robot joint.

The invention is based on the realization that condition monitoring of industrial robots can make a direct use of the repetitive behavior of the system when the monitored quantity is suitable. A difference between distributions of torque measurements taken under recurring conditions is found out to be such suitable quantity.

According to a first aspect of the invention, there is provided a method for detecting a fault in a robot joint. The method comprises the steps of: performing a first torque measurement at the robot joint to thereby obtain a first set of torque values; calculating a first distribution characteristic reflecting a distribution of the first set of torque values; performing a second torque measurement at the robot joint to thereby obtain a second set of torque values; calculating a second distribution characteristic reflecting a distribution of the second set of torque values; and comparing the first and the second distribution characteristics to determine whether a fault is present or not. A difference between distributions of two torque measurements is found out to be a good fault indicator for machine parts executing repetitive tasks.

According to one embodiment of the invention, the first distribution characteristic comprises a first distribution function, and the second distribution characteristic comprises a second distribution function. The method further comprises the step of calculating a difference between the first and the second distribution functions to thereby obtain a first difference to determine whether a fault is present or not. A difference between distribution functions from two torque measurements is found out to be a good fault indicator for machine parts executing repetitive tasks.

According to one embodiment of the invention, the method further comprises the steps of: performing a third torque measurement at the robot joint to thereby obtain a third set of torque values; calculating a third distribution function reflecting a distribution of the third set of torque values; calculating a difference between the second and the third distribution functions to thereby obtain a second difference; and calculating a sum of the first difference and the second difference to determine whether a fault is present or not. A sum of differences between two pairs of distribution functions from torque measurements is found out to be a good fault indicator for machine parts executing repetitive tasks.

According to one embodiment of the invention, the first and second distribution functions are kernel density estimators, and the first difference is calculated using a distance measure such as Kullback-Leibler distance. A difference between kernel density estimators from two torque measurements is found out to be a good fault indicator for machine parts executing repetitive tasks.

According to one embodiment of the invention, the method further comprises the step of, before calculating the first and second distribution characteristics, eliminating from the first and the second sets of torque values those values that are obtained at a joint speed under a first threshold value and/or at a joint speed over a second threshold value to thereby obtain a first set of filtered torque values and a second set of filtered torque values. By filtering out torque values obtained at low and/or high joint speeds, an even better fault indicator is achieved since an optimal region for wear monitoring is concentrated in a narrow joint speed range.

According to one embodiment of the invention, the method further comprises the steps of: calculating a mean value of the first set of filtered torque values to thereby obtain a first distribution mean value; calculating a mean value of the second set of filtered torque values to thereby obtain a second distribution mean value; and calculating a difference between the first and the second distribution mean values to determine whether a fault is present or not. A mean value is a distribution characteristic that is found out to provide a good fault indicator according to the method of the present invention.

According to one embodiment of the invention, the first measurement is performed during a first task executed by the robot joint, and the second measurement is performed during a second task executed by the robot joint, the first task being executed earlier than the second task. In order to provide a fault indicator according to the present invention, the torque measurements need to be performed at different times.

According to one embodiment of the invention, the first and the second tasks are identical. In order to provide a fault indicator according to the present invention, the torque measurements need to be performed during comparable robot movements.

According to one embodiment of the invention, the first task is executed when the robot joint is new or it is otherwise known that a fault is not present. This assumption facilitates the detection of the fault indicator.

According to one embodiment of the invention, the first and the second sets of torque values are weighted by means of a weighting vector. By this measure the fault indicator can be further amplified.

According to one embodiment of the invention, the first and the second distribution functions are weighted by means of a weighting function. By this measure the fault indicator can be further amplified.

According to one embodiment of the invention, the weighting function has joint speed as an input. Joint speed is found out to have a strong impact on the torque measurement results, and this impact can be reduced by an appropriate weighting function taking the joint speed into account.

According to one embodiment of the invention, the first torque measurement is performed at a first joint temperature, and the second torque measurement is performed at a second joint temperature, the first joint temperature being identical with the second joint temperature. Joint temperature is found out to have a strong impact on the torque measurement results, and this impact can be reduced by performing the measurements in comparable temperature conditions.

BRIEF DESCRIPTION OF THE DRAWINGS

The invention will be explained in greater detail with reference to the accompanying drawings, wherein.

DETAILED DESCRIPTION OF THE INVENTION

Figure 1:
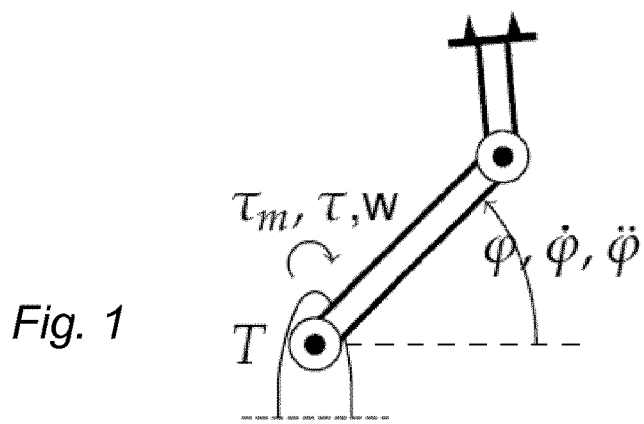
FIG. 1 shows a schematic illustration of an industrial robot.
Figure 2A:
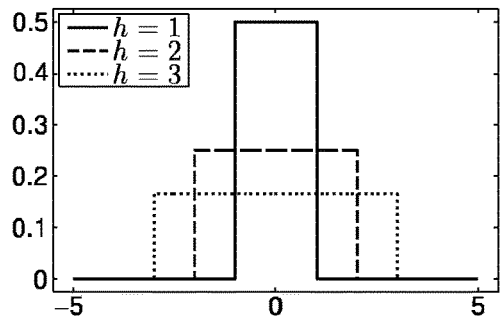
FIGS. 2a-2f show some kernel functions and their respective Fourier transforms.
Figure 2B:
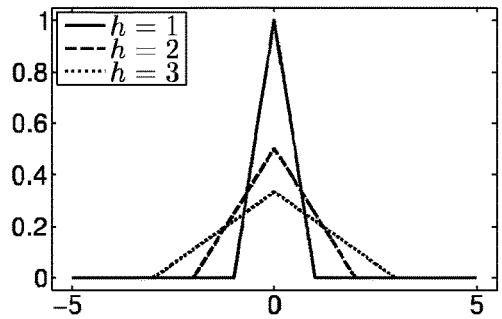
Figure 2C:
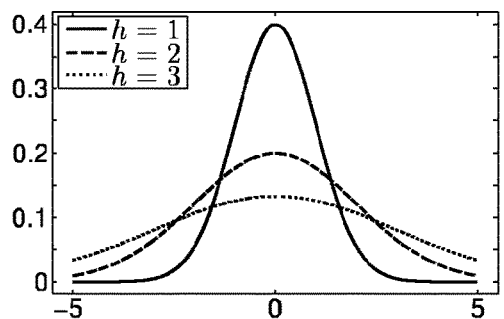
Figure 2D:
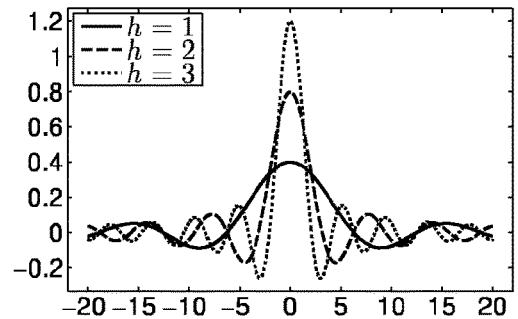
Figure 2E:
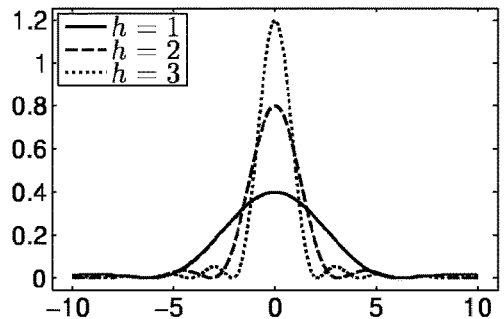
Figure 2F:
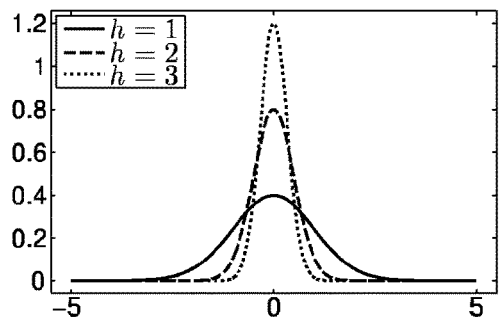

Referring to FIG. 1, an industrial robot can be described as a multi body dynamic mechanism by $$\tau = M(\varphi)\ddot{\varphi} + C(\varphi,\dot{\varphi}) + D\dot{\varphi} + \tau_g(\varphi) + \tau_s(\varphi) + \tau_f(\dot{\varphi},\tau_m,T,w), \quad (1)$$

where $\tau$ is torque at a robot joint, $\varphi$ is an angular joint position of the robot joint, $M(\varphi)$ is an inertia vector, $C(\varphi,\dot{\varphi})$ relates to speed dependent terms (e.g. Coriolis and centrifugal), D is a damping vector, $\tau_g(\varphi)$ is a gravity-induced torque, $\tau_s(\varphi)$ is a nonlinear stiffness. The function $\tau_f(\dot{\varphi}, \tau_m, T, w)$ contains the joint friction components and is dependent on joint speed $\dot{\varphi}$, the load torque $\tau_m$ caused by the manipulated load, the joint temperature T and the wear level w.

The deterministic input of interest is the wear level w, which is zero when the robot is new and increases with time/usage. When the wear level w exceeds a predetermined threshold value, it is considered as a fault. Since from equation (1) it is obvious that the torque T is affected directly by the wear level w, the torque $\tau$ is apparently a quantity of interest and is to be measured. The remaining variables, the joint position $\varphi$ and its derivatives, the load torque $\tau_m$ and the joint temperature T, are considered as disturbances. In order to be able to exclude the effects of these disturbances, it may be advantageous to measure especially the joint position/speed $\varphi/\dot{\varphi}$ and the joint temperature T as well.

The torque $\tau$ is measured during a task $\mathcal{U}$ executed by the robot, and a set of N measured torque values is obtained to constitute an N-dimensional torque vector, $$\tau^j = [\tau_1^j, \ldots, \tau_N^j]^T,$$

where $\tau_i^j$ denotes an individual torque value. A task $\mathcal{U}$ comprises a known movement or a sequence of movements of the robot joint at which the measurement is performed, the angular position $\varphi$ of the robot joint changing in a known manner during a task $\mathcal{U}$. The measurement is repeated M times, during execution of M tasks $\mathcal{U}$, whereby the measurement data constitutes an N×M torque matrix, $$T^M = [\tau^0, \ldots, \tau^j, \ldots, \tau^{M-1}],$$

where $\tau^0$ is a nominal torque vector representing data with zero wear level w.

According to one embodiment of the invention, for the purpose of monitoring the torque $\tau$ to detect changes in wear level w, the following assumptions are taken:

Assumption 1: Regularity of $\tau^j$ if no fault. It is considered that the measured torque $\tau^j$ change only slightly along j, unless in the presence of a nonzero wear level $w^j$.

Assumption 2: Faults are observable. Changes on wear level $w^j$ affect the measured torque $\tau^j$.

Assumption 3: Nominal data is available. At j=0, wear level $w^0=0$, and the nominal torque vector $\tau^0$ is always available.

According to one embodiment of the invention, the nominal torque vector $\tau^0$ (always available from Assumption 3) is compared against the remaining torque vectors $\tau^j$. While Assumption 2 is necessary, Assumption 1 ensures that two given torque vectors $\tau^i$ and $\tau^j$ are comparable and might differ significantly only if there is a fault.

The effects of the angular position $\varphi$, its derivatives, and the load torque $\tau_m$ are defined by the task $\mathcal{U}$. Therefore, if two torque vectors $\tau^i$ and $\tau^j$ are obtained from two identical tasks $\mathcal{U}$, these disturbances are not an obstacle to satisfy Assumption 1. If also the joint temperature T is identical during the two identical tasks $\mathcal{U}$, then the torque vectors $\tau^i$ and $\tau^j$ satisfy the Assumption 1 and the framework is valid. The joint temperature T is however the result of complicated losses mechanisms in the robot joint and heat exchanges with the environment and might cause the Assumption 1 not to be satisfied. The effect of the joint temperature T on the torque $\tau$ is in fact comparable to that caused by the wear level w. The problem of robust monitoring of the wear level w is therefore challenging.

The torque vectors $\tau^j$ need to be characterized in an appropriate way in order to render two torque vectors $\tau^i$ and $\tau^j$ comparable for the purpose of detecting a fault in the robot joint. There are several ways to characterize a torque vector $\tau^j$. It could be represented by a single number, such as its mean, peak, range, etc. Summarizing the whole torque vector $\tau^j$ into a single quantity might however hide many of the torque vector's $\tau^j$ features. A second alternative would be to simply store the whole torque vector $\tau^j$ and try to monitor the difference $\tau^0 - \tau^j$, but this requires that the torque vectors $\tau^0$ and $\tau^j$ are synchronized, which is a limitation in many applications. Sometimes, looking at the data spectra is helpful, but this type of analysis requires the data to be ordered.

The alternative according to the present invention is to consider the distribution of the torque vector $\tau^j$, which does not require ordering or synchronization and reveals many of the torque vector's $\tau^j$ features.

Because the mechanisms that generate the torque vector $\tau^j$ are considered unknown, the use of a nonparametric estimate of the distribution $\hat{p}(\cdot)$ of the torque vector $\tau^j$ is a suitable alternative. Such estimate can be obtained with the use of kernel density estimators, $$\hat{p}^j(\tau) = N^{-1} \sum_{i=1}^{N} k_h(\tau - \tau_i^j), \quad (2)$$

where $k_h(\cdot)$ is a kernel function, satisfying $k_h(\cdot) \geq 0$ and that integrates to 1 over $\mathbb{R}$. The bandwidth $h > 0$ is a smoothing parameter and $\tau$ includes the domain of $T^M$. From the definition, it follows that $\int \hat{p}(\tau) d\tau = 1$, that is, the distribution is normalized to 1.

The operation according to the equation (2) can be rewritten as the convolution $$\hat{p}^j(\tau) = N^{-1} \int_{-\infty}^{\infty} \sum_{i=1}^{N} \delta(x - \tau_i^j) k_h(\tau - x) dx, \quad (3)$$

where $\delta(\cdot)$ is the Dirac delta. Using the convolution theorem, the kernel density estimator can be seen as a filter in the frequency domain, controlling the smoothness of the estimated distribution. It is typical to choose kernel functions with a low pass behavior, where the bandwidth parameter h controls its cutoff frequency. Typical kernel functions (left column) and their Fourier transforms (right column) are shown in FIG. 2.

Figure 3A:
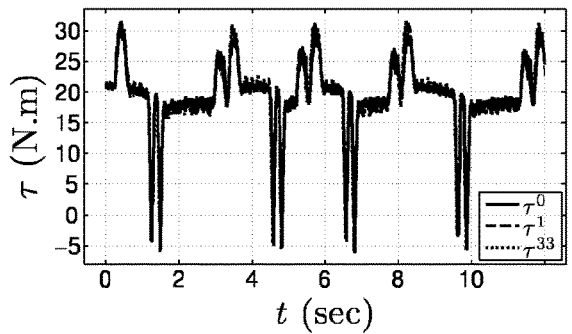
FIGS. 3a-3b show measured torque signals and their respective kernel density estimators for a tested robot joint.
Figure 3B:
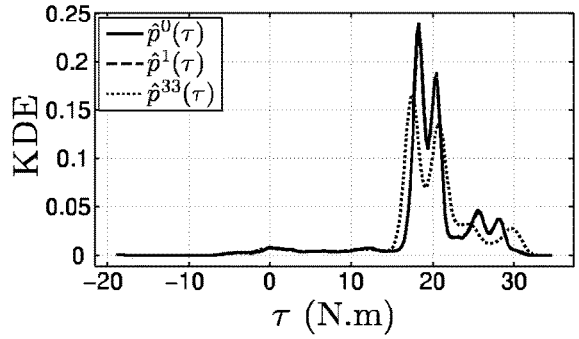

FIG. 3 shows results of a wear test (Wear Test 1) performed at a robot joint with the objective of studying the wear effects. During the test, the joint temperature T is kept constant and torque vectors $\tau^j$ corresponding to the torque signals shown in FIG. 3a are obtained from identical tasks $\mho$ so that Assumption 1 is satisfied. The measurement is repeated for identical tasks $\mho$ executed regularly a total of M=33 times yielding a torque matrix $T^M = [\tau^0, \ldots, \tau^j, \ldots, \tau^{M-1}]$. The tests are executed until the wear levels are considered significant, so that maintenance should be performed. The torque signals corresponding to the torque vectors $\tau^0$, $\tau^1$ and $\tau^{33}$ are shown in FIG. 3a, and the corresponding kernel density estimators are shown in FIG. 3b. The torque vectors $\tau^0$ and $\tau^1$ are considered to represent a new and a substantially new robot joint, respectively, while the torque vector $\tau^{33}$ represents a robot joint with increased wear level w. The kernel density estimators are close to identical for the torque vectors $\tau^0$ and $\tau^1$, and differ considerably from the kernel density estimators of the torque vector $\tau^{33}$. The results according to FIG. 3 show that Assumptions 1 and 2 are valid, and that it is possible to detect a fault by monitoring the changes in the kernel density estimators.

In statistics and information theory, the Kullback-Leibler divergence (KLD) is one of the methods used to measure the difference between two probability distributions. For two continuous distributions on x, p(x) and q(x), it is defined as $$D_{KL}(p\|q) = -\int_{-\infty}^{\infty} p(x) \log \frac{q(x)}{p(x)} dx, \quad (4)$$

wherein $q(x) > 0$ for any x such that $p(x) > 0$. The KLD satisfies $D_{KL}(p\|q) \geq 0$ (Gibbs inequality), with equality if and only if $p(x) = q(x)$. The KLD is in general not symmetric, $D_{KL}(p\|q) \neq D_{KL}(q\|p)$. The quantity $$KL(p\|q) \triangleq D_{KL}(p\|q) + D_{KL}(q\|p), \quad (5)$$

known as the Kullback-Leibler distance (KL distance), is however symmetric. Although the KL distance is defined for probability functions, it can also be used for kernel density estimators since they are normalized to 1. The torque vectors $\tau^j$ can consequently be characterized with the help of a KL distance in order to render two torque vectors $\tau^j$ and $\tau^l$ comparable for the purpose of detecting a fault in the robot joint. From Assumption 3 it follows that nominal data is available, so that the nominal torque vector $\tau^0$ is known and $\hat{p}^0(\tau)$ can be evaluated. The quantities $KL(\hat{p}^0\|\hat{p}^j)$ can therefore be used as a fault indicator.

Figure 4A:
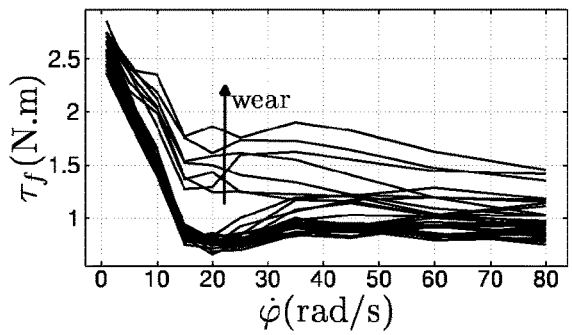
FIGS. 4a-4d show friction curves and three different fault indicators according to the invention for a tested robot joint.
Figure 4B:
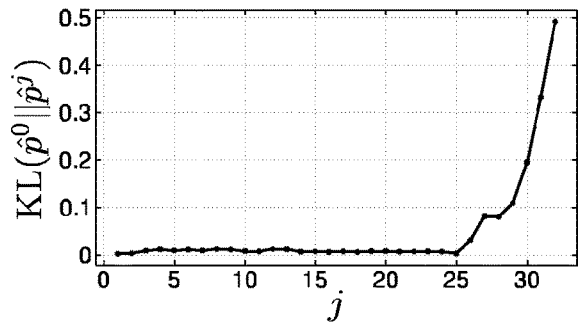

Using the torque matrix $T^M = [\tau^0, \ldots, \tau^j, \ldots, \tau^{M-1}]$ obtained from the Wear Test 1, the respective kernel density estimators are computed, resulting in $[\hat{p}^0(\tau), \ldots, \hat{p}^j(\tau), \ldots, \hat{p}^{M-1}(\tau)]$, wherein $\hat{p}^0(\tau)$ represents a new fault free robot joint. The quantities $KL(\hat{p}^0\|\hat{p}^j)$ are computed for j=1, ..., M-1. As shown in FIG. 4b, these quantities show a clear response to the increased wear level w and can therefore be used as a fault indicator. For an illustration of the wear behavior during the experiments, the friction curves in the joint were estimated using a dedicated experiment at each execution of a task $\mho$ and are shown in FIG. 4a.

The above example illustrates how the basic framework according to the invention can be successfully used to monitor a robot joint that operates in a repetitive manner. The regularity requirement according to Assumption 1 is, however, limiting in many practical applications. Further embodiments of the invention are therefore adopted with the aim of relaxing the Assumption 1.

Since $KL(\hat{p}^{j-1}\|\hat{p}^j)$ measures the difference between the kernel density estimators of consecutive torque vectors $\tau^{j-1}$ and $\tau^j$, the sum of these increments over 1, ..., j gives the accumulated changes up to j, which is related to a fault and can therefore be used for monitoring.

Because of measurement noise, the increments $KL(\hat{p}^{j-1}\|\hat{p}^j)$ will also have a random behavior when there is no fault. The simple summation of the increments will therefore behave like a random walk and drift away. An alternative is to use a cumulative sum (CUSUM) algorithm, defined as $$g^j = g^{j-1} + s^j - \nu \quad (6)$$

$$g^j = 0 \text{ if } g^j < 0 \quad (7)$$

The test statistic $g^j$ adds up the signal to be monitored $s^j$, which in the context presented here is $s^j = KL(\hat{p}^{j-1}\|\hat{p}^j)$. To avoid positive drifts, a subtracted drift parameter $\nu$ is included in the equation (6). Negative drifts are avoided by resetting $g^j$ according to equation (7) if the outcome of equation (6) is negative. The resulting quantity $g^j$ is suitable for condition monitoring and does not require assignment of a nominal data, that is, Assumption 3 is relaxed. The drift parameter can be chosen as $$\nu = \kappa \sigma + \mu, \quad (8)$$

where $\mu$ and $\sigma$ are the mean and the standard deviation of the increments $KL(\hat{p}^{j-1}\|\hat{p}^j)$ under no fault, and $\kappa$ is a positive constant.

Figure 4C:
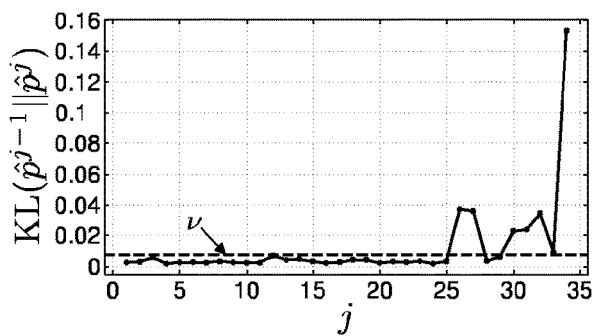
Figure 4D:
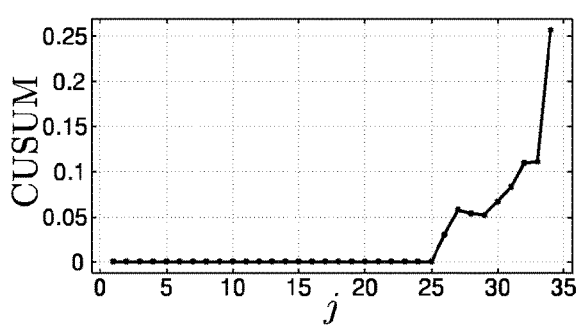

The Wear Test 1 is considered again. Instead of using $KL(\hat{p}^0\|\hat{p}^j)$ as a fault indicator, the increments $KL(\hat{p}^{j-1}\|\hat{p}^j)$ are computed and the CUSUM algorithm is used. The drift parameter is chosen according to equation (8), with $\kappa = 3$ and $\mu$ and $\sigma$ estimated from the first 5 sequences. The resulting quantities are shown FIGS. 4c and 4d, which show a clear response to the increase of the wear level w.

Let $\mho^j$ denote the task under which a torque vector $\tau^j$ is generated. Assumption 1 requires the whole torque matrix $T^M$ to have been generated under the same task $\mho$ to be comparable. The alternative solution of monitoring the accumulated consecutive increments $KL(\hat{p}^{j-1}\|\hat{p}^j)$ requires, in principle, that only $\mho^{j-1}$ and $\mho^j$ are the same, thereby relaxing Assumption 1.

Since the behavior of the increments might differ depending on the task $\mho$, special care should be taken when monitoring their accumulated changes. If the CUSUM algorithm is used, the drift parameter $v$ can be set differently according to the executed task, that is, $v$ will be a function of $\mho$.

An alternative to achieve robustness to disturbances is to consider weighting the raw data according to prior knowledge of the fault and disturbances. Defining a weighting vector $\Omega \in \mathbb{R}^N$, the weighted torque data can be written as $$\bar{\tau}^j = \Omega \circ \tau^j, \qquad (9)$$

where $\circ$ is the Hadamard product (element-wise multiplication). The idea is to choose the weighting vector $\Omega$ to maximize the sensitivity to faults while increasing the robustness to disturbances.

Considering the basic framework presented above, a natural criterion for weighting vector $\Omega$ would be to choose it such that $\mathrm{KL}(\hat{p}^j(\Omega) \| \hat{p}^l(\Omega))$ is maximized when $\bar{\tau}^j$ represents a fault free robot joint and $\bar{\tau}^l$ represents a faulty robot joint, and it is minimized in case $\bar{\tau}^j$ and $\bar{\tau}^l$ both represent a fault free or faulty robot joint. A general solution to this problem is however difficult since it depends on how $\hat{p}^j(\Omega)$ was computed (e.g. the kernel function chosen). In the following, simpler criteria are used in a compromise of explicit solutions. As it will be shown, the results are directly related to linear discriminant analyses.

Consider that the torque matrix $T^M$ is available and the fault status (present or not) is known for each torque vector $\tau^j$, and the fault status is the same for each element in each torque vector $\tau^j$. The data representing a fault free status are said to belong to the class $C_0$, with $M_0$ observations, while the data representing a faulty status belong to class $C_1$, with $M_1 = M - M_0$ observations. Applying the weighting vector $\Omega$ to the torque matrix $T^M$ yields $$\bar{T}^M \triangleq [\bar{\tau}^0, \ldots, \bar{\tau}^{M_0+1}, \ldots, \bar{\tau}^{M_1+M_0}], \qquad (10)$$

and the objective is to choose $\Omega$ such that the separation between the classes is maximized. A simple criterion is to consider the difference between the classes' means $\bar{m}$. The kth class mean $\bar{m}^k$ over all $M_k$ observations is $$\bar{m}^k \triangleq \qquad (11)$$

$$N^{-1} \sum_{i=0}^{N-1} \left[ M_k^{-1} \sum_{j \in C_k} \omega_i \tau_i^j \right] = N^{-1} \sum_{i=0}^{N-1} \omega_i \underbrace{\left[ M_k^{-1} \sum_{j \in C_k} \tau_i^j \right]}_{\triangleq m_i^k} = N^{-1} \Omega^T m^k.$$

The distance between the means of classes $C_0$ and $C_1$ is proportional to $$\bar{m}^1 - \bar{m}^0 \propto \Omega^T(m^1 - m^0) \qquad (12)$$

This problem is equivalently found in linear discriminant analyses. Constraining $\Omega$ to unit length in order to achieve a meaningful solution, it is easy to see that the optimal choice is to take $\Omega \propto (m^1 - m^0)$.

A criterion based only on the distance between the classes' means $\bar{m}$ does not consider the variability found within each class $C_0$, $C_1$, for instance caused by disturbances. An alternative is to consider maximum separation between the classes' means $\bar{m}$ while giving small variability within each class $C_0$, $C_1$. Considering a measure of variability for each class $C_0$, $C_1$ as the mean of variances for each ith component, $$\bar{s}^k \triangleq N^{-1} \sum_{i=0}^{N-1} \left[ M_k^{-1} \sum_{j \in C_k} (\omega_i \tau_i^j - \omega_i m_i^k)^2 \right] = \qquad (13)$$

$$N^{-1} \sum_{i=0}^{N-1} \omega_i^2 \underbrace{\left[ M_k^{-1} \sum_{j \in C_k} (\tau_i^j - m_i^k)^2 \right]}_{\triangleq s_i^k} = N^{-1} \Omega^T S^k \Omega,$$

where $S^k$ is a diagonal matrix with diagonal elements given by $s_i^k$. Defining the total within class variation as $\Sigma_k \bar{s}^k$, the following criterion can be used when two classes are considered $$\frac{(\bar{m}^1 - \bar{m}^0)^2}{\bar{s}_1 + \bar{s}_0} \propto \frac{\Omega^T(m^1 - m^0)(m^1 - m^0)^T \Omega}{\Omega^T(S^1 + S^0)\Omega}, \qquad (14)$$

which is a special case of the Fisher criterion. It can be shown that solutions for this problem satisfy $$\Omega \propto (S^1 + S^0)^{-1}(m^1 - m^0). \qquad (15)$$

That is, each weight $\omega_i$ is proportional to the ratio between the average changes $m_i^1 - m_i^0$ and the total variability found in the data $s_i^1 + s_i^0$.

Notice however that the solutions according to the equations (12) and (15) require the data to be synchronized, which is difficult in many practical applications. In case this is possible (for instance using simulations), the result of such analyses might reveal some useful pattern of the weights $\omega_i$. For instance, if the weights $\omega_i$ are strongly correlated to measured data, an approximate function can be used to describe the weights $\omega_i$ depending on the data, e.g. $\omega_i = h(\tau_i^j)$ for a continuous function $h(\bullet)$.

To illustrate the ideas presented hereinbefore, a simulation study is carried out. A task $\mho$ is simulated $M = M_1 + M_0$ times under different conditions, forming a torque matrix $T^M$, with $M_1 = M_0 = 100$. A realistic friction model is used that represents the effects of the wear level $w$ and joint temperature $T$.

The two sets of data are generated with the following settings $$\tau^i : w = 0, T \sim \mathcal{U}[\underline{T}, \underline{T} + \Delta_T], i \in C_0 \qquad (16a)$$

$$\tau^l : w = w_c, T \sim \mathcal{U}[\underline{T}, \underline{T} + \Delta_T], l \in C_1 \qquad (16b)$$

where $i \in C_0$ corresponds to the first $M_0$ simulations and $l \in C_1$ the remaining ones, $w_c = 35$ is a wear level considered critical to generate an alarm. The unit of the wear level $w$ can be considered to be percentage %, where 0% represents a new robot joint, and 100% represents a totally worn out robot joint. Here, the joint temperature $T$ is considered random, with uniform distribution given by $\underline{T} = 30°$ C. and $\Delta_T = 40°$ C. This assumption is carried out for analyses purposes.

Figure 5A:
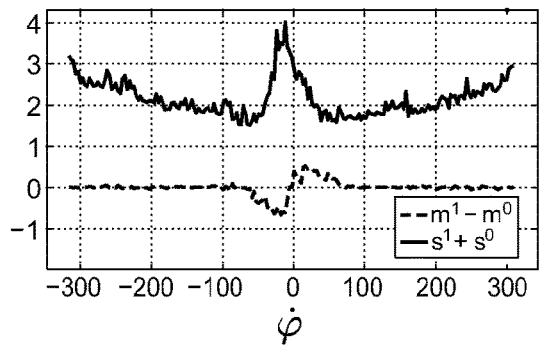
FIGS. 5a-5b show worst case estimates for an average distance and a total variability between two sets of data as a function of joint speed $\dot{\varphi}$, and the respective optimal weights for a tested robot joint.
Figure 5B:
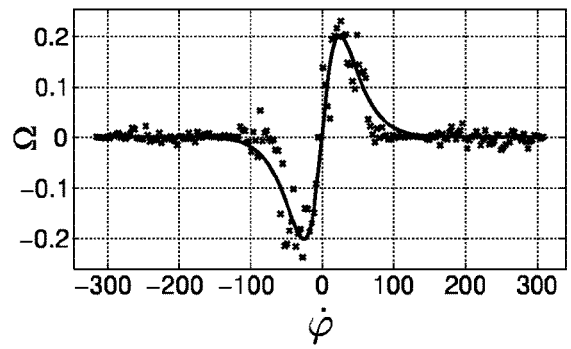

Worst case estimates, average distance $m_i^1 - m_i^0$ closest to zero and largest total variability $s_i^1 + s_i^0$, respectively, are displayed as a function of the joint speed $\dot{\varphi}$ in FIG. 5$a$. FIG. 5$b$ presents the ratio for such worst case estimate, which is considered as the optimal weights according to equation (15). As it can be seen, the optimal weights present a strong correlation with joint speed $\dot{\varphi}$, which is not a surprise since the effects of wear level $w$ and joint temperature $T$ depend on the joint speed $\dot{\varphi}$ as established before. The optimal region for wear monitoring is concentrated in a narrow speed range. The solid line in FIG. 5b is a function approximation of the optimal weights given by $$\omega(\dot{\varphi}) = \text{sech}(\beta\dot{\varphi})\tan h(\alpha\dot{\varphi}) \quad (17)$$

with $\alpha=1.45\times10^{-2}$ and $\beta=4.55\times10^{-2}$. Effectively, the optimal weighting function selects a joint speed region that is more relevant for robust wear monitoring.

The performance improvements achieved using the weighting function can be illustrated by considering the detection of an abrupt change of the wear level w from 0 to $w_c$. Considering a data set generated according to equations (16a) and (16b), a pair $(\tau''', \tau'')$ is given, and the objective is to decide whether the pair is from the same class or not, that is, the two hypotheses $\mathcal{H}_0$, $\mathcal{H}_1$ are considered $$\mathcal{H}_0: m, n \in C_0 \text{ or } m, n \in C_1 \quad (18a)$$

$$\mathcal{H}_1: m \in C_0, n \in C_1 \text{ or } m \in C_1, n \in C_0 \quad (18b)$$

In view of the framework presented hereinbefore, this problem is analyzed by computing the distribution of $KL(\hat{p}'''\|\hat{p}'')$ for each hypothesis.

Figure 6A:
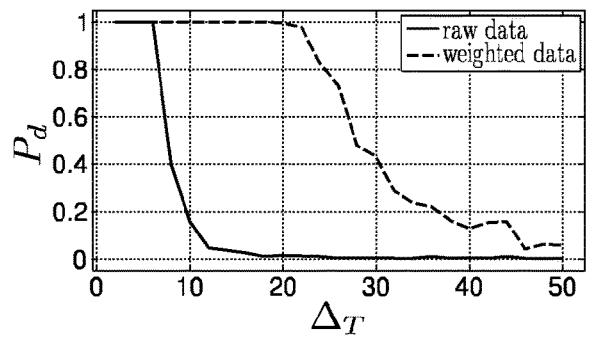
FIGS. 6a-6b illustrate an improved probability of fault detection $P_d$ with weighted data.

The overlap of these distributions gives a probability of false alarm $P_f$, and a probability of fault detection $P_d$ (the problem is a binary hypothesis test). The procedure is repeated for different values of $\Delta_T$, with and without the use of the weighting function. For the fixed $P_f=0.01$, FIG. 6a presents the achieved $P_d$ as a function of $\Delta_T$. Notice that the use of the weighting function considerably improves the robustness to temperature variations, but for too large $\Delta_T$ it becomes difficult to distinguish the effects.

Figure 6B:
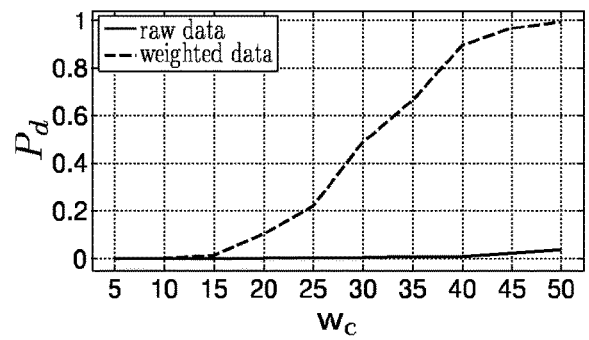

A similar study can be performed to illustrate how $w_c$ affects the performance. For the fixed $\Delta_T=25°$ C., data are generated according to equations (16a) and (16b) for different values of $w_c$. Similarly, the hypotheses distributions are computed. FIG. 6b presents $P_d$ as a function of $w_c$ for the fixed $P_f=0.01$. The improvements achieved using the weighted data are obvious.

The invention is not limited to the embodiments shown above, but the person skilled in the art may modify them in a plurality of ways within the scope of the invention as defined by the claims. Thus, the invention is not limited to detecting faults in robot joints, but may also be applied to any machine parts executing repetitive tasks.

What is claimed is:

1. A method for detecting a fault in a robot joint, the method comprising the steps of:
performing a first torque measurement at the robot joint to obtain a first set of torque values and weighting each individual torque value of the first set of torque values by means of a weighting vector to thereby obtain a first set of weighted torque values, the weighting vector having a set of different weights so that the first set of weighted torque values reflects torque magnitudes in time domain;
calculating a first distribution characteristic reflecting a distribution of the first set of weighted torque values;
performing a second torque measurement at the robot joint to obtain a second set of torque values and weighting each individual torque value of the second set of torque values by means of the weighting vector to thereby obtain a second set of weighted torque values reflecting torque magnitudes in time domain;
calculating a second distribution characteristic reflecting a distribution of the second set of weighted torque values;
comparing the first and the second distribution characteristics to determine whether a fault is present or not; and
performing maintenance on the robot joint when it is determined that a fault is present.

2. The method according to claim 1, wherein the first distribution characteristic comprises a first distribution function, and the second distribution characteristic comprises a second distribution function, the method further comprising the step of:
calculating a difference between the first and the second distribution functions to thereby obtain a first difference to determine whether a fault is present or not.

3. The method according to claim 2, the method further comprising the steps of:
performing a third torque measurement at the robot joint to thereby obtain a third set of torque values;
weighting each individual torque value of the third set of torque values to thereby obtain a third set of weighted torque values;
calculating a third distribution function reflecting a distribution of the third set of weighted torque values;
calculating a difference between the second and the third distribution functions to thereby obtain a second difference; and
calculating a sum of the first difference and the second difference to determine whether a fault is present or not.

4. The method according to claim 3, wherein the first and second distribution functions are kernel density estimators, and the first difference is calculated using a distance measure such as Kullback-Leibler distance.

5. The method according to claim 2, wherein the first and second distribution functions are kernel density estimators, and the first difference is calculated using a distance measure such as Kullback-Leibler distance.

6. The method according to claim 2, wherein the first and the second distribution functions are weighted by means of a weighting function.

7. The method according to claim 6, wherein the weighting function has joint speed as an input.

8. The method according to claim 1, the method further comprising the step of:
before calculating the first and second distribution characteristics, eliminating from the first and the second sets of weighted torque values those values that are obtained at a joint speed under a first threshold value and/or at a joint speed over a second threshold value to thereby obtain a first set of filtered torque values and a second set of filtered torque values.

9. The method according to claim 5, the method further comprising the steps of:
calculating a mean value of the first set of filtered torque values to thereby obtain a first distribution mean value;
calculating a mean value of the second set of filtered torque values to thereby obtain a second distribution mean value; and
calculating a difference between the first and the second distribution mean values to determine whether a fault is present or not.

10. The method according to claim 1, wherein the first measurement is performed during a first task executed by the robot joint, and the second measurement is performed during a second task executed by the robot joint, the first task being executed earlier than the second task.

11. The method according to claim 10, wherein the first and the second tasks are identical.

12. The method according to claim 11, wherein the first task is executed when the robot joint is new or it is otherwise known that a fault is not present.

13. The method according to claim 10, wherein the first task is executed when the robot joint is new or it is otherwise known that a fault is not present.

14. The method according to claim 1, wherein the first torque measurement is performed at a first joint temperature, and the second torque measurement is performed at a second joint temperature, the first joint temperature being identical with the second joint temperature.

15. The method according to claim 1, wherein the comparing comprises comparing distributions of the first and second sets of weighted torque values.

16. A method for detecting a fault in a robot joint, the method comprising the steps of:
    performing a first torque measurement at the robot joint to obtain a first set of torque values and weighting each individual torque value of the first set of torque values by means of a weighting vector to thereby obtain a first set of weighted torque values, the weighting vector having a set of different weights so that the first set of weighted torque values reflects torque magnitudes in time domain;
    calculating a first distribution characteristic reflecting a distribution of the first set of weighted torque values;
    performing a second torque measurement at the robot joint to obtain a second set of torque values and weighting each individual torque value of the second set of torque values by means of the weighting vector to thereby obtain a second set of weighted torque values reflecting torque magnitudes in time domain;
    calculating a second distribution characteristic reflecting a distribution of the second set of weighted torque values;
    comparing the first and the second distribution characteristics to determine whether a fault is present or not; and
    performing maintenance on the robot joint when it is determined that a fault is present;
    wherein the weighting individual torque values amplifies an indicator of whether a fault is present or not.

17. A method for detecting a fault in a robot joint, the method comprising the steps of:
    performing a first torque measurement at the robot joint to obtain a first set of torque values;
    calculating a first distribution function reflecting a distribution of the first set of torque values using a weighting function;
    performing a second torque measurement at the robot joint to obtain a second set of torque values;
    calculating a second distribution function reflecting a distribution of the second set of torque values using the weighting function;
    calculating a difference between the first and the second distribution functions to determine whether a fault is present or not; and
    performing maintenance on the robot joint when it is determined that a fault is present;
    wherein the weighting function has joint speed as an input.

* * * * *